United States Patent [19]

Florvall et al.

[11] 4,000,280
[45] Dec. 28, 1976

[54] PHARMACEUTICAL COMPOSITIONS CONTAINING AN AMPHETAMINE DERIVATIVE FOR THE ALLEVIATION OF ANXIETY OR TREATMENT OF DEPRESSION

[75] Inventors: Gösta Lennart Florvall; Svante Bertil Ross; Sven-Ove Ögren, all of Sodertalje, Sweden

[73] Assignee: Astra Lakemedel Aktiebolag, Sodertalje, Sweden

[22] Filed: June 30, 1975

[21] Appl. No.: 592,082

Related U.S. Application Data

[62] Division of Ser. No. 497,295, Aug. 14, 1974.

[52] U.S. Cl. .................................... 424/258
[51] Int. Cl.$^2$ ................................. A61K 31/47
[58] Field of Search ............................ 424/258

[56] References Cited

OTHER PUBLICATIONS

Rachinskii–Chem. Abst., vol. 56 (1962) pp. 5928 & 5929.
Richards–Chem. Abst., vol. 72 (1970) p. 21713m.

*Primary Examiner*—Sam Rosen
*Attorney, Agent, or Firm*—Brumbaugh, Graves, Donohue & Raymond

[57] ABSTRACT

Compounds having the general formula

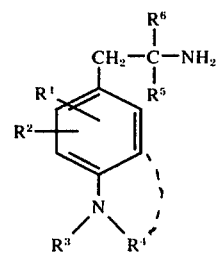

I or pharmaceutically acceptable salts thereof, in which formula $R^1$ and $R^2$ are the same or different and each represents a hydrogen atom, a lower alkyl group or a halogen atom, $R^3$ represents a lower alkyl group or a benzyl group, $R^4$ represents a hydrogen atom, a lower alkyl group, a benzyl group or a $CH_2CH_2CH_2$-bridge connected to the phenyl ring in ortho-position relative to the N-substituent, $R^5$ represents a hydrogen atom or a methyl group and $R^6$ represents a lower alkyl group, provided that $R^1$ and/or $R^2$ represents a lower alkyl group or a halogen atom where $R^3$ represents a methyl group, $R^4$ represents a methyl group and $R^5$ represents a hydrogen atom; methods for the preparation thereof; intermediates useful for their preparation; pharmaceutical preparations containing at least one of these compounds; and the use thereof in the treatment of depressive states and alleviating anxiety.

6 Claims, No Drawings

PHARMACEUTICAL COMPOSITIONS CONTAINING AN AMPHETAMINE DERIVATIVE FOR THE ALLEVIATION OF ANXIETY OR TREATMENT OF DEPRESSION

This is a division of our copending application Ser. No. 497,295 filed Aug. 14, 1974.

This invention relates to new 4-aminoamphetamine derivatives and to methods for their preparation as well as to new intermediates useful for the preparation of the 4-aminoamphetamine derivatives. The invention also relates to the preparation of pharmaceutical preparations containing the 4-aminoamphetamine derivatives and to methods for their pharmacological use.

PRIOR ART

Depressive disorders have with more or less success been treated with various compounds. Many types of chemical substances have been used, among these amphetamine with the structure

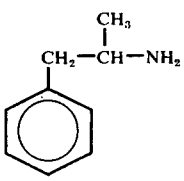

However, the euphoretic effect and the risk of dependence have to a great extent restricted the use of amphetamine in such therapy.

The medical use of amphetamine is nowadays mainly restricted to the treatment of narcolepsy and asthenic states in aged people.

OUTLINE OF INVENTION a. General outline

We have found that by proper substitution of amphetamine the euphoric or central stimulant effect of the substance can be diminished or completely abolished. The pharmacological profile of the compounds of the invention suggests a potential value of the compounds as antidepressants and also as a new type of anxiolytics.

The compounds of the invention are characterized by the general formula

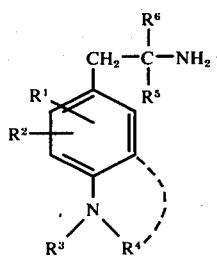

I or a pharmaceutically acceptable salt thereof, in which formula $R^1$ and $R^2$ are the same or different and each represents a hydrogen atom, a lower alkyl group of a halogen atom, $R^3$ represents a lower alkyl group or a benzyl group, $R^4$ represents a hydrogen atom, a lower alkyl group, a benzyl group or a $CH_2CH_2CH_2$-bridge connected to the phenyl ring in ortho-position relative to the N-substituent, $R^5$ represents a hydrogen atom or a methyl group and $R^6$ represents a lower alkyl group, provided that $R^1$ and/or $R^2$ represents a lower alkyl group or a halogen atom when $R^3$ represents a methyl group, $R^4$ represents a methyl group and $R^5$ represents a hydrogen atom.

Illustrative examples of radicals included in the above definitions are lower alkyl group: methyl, ethyl, n-propyl and isopropyl halogen atom: chlorine, bromine, iodine and fluorine.

By the expression "lower alkyl group" in this application is to be understood alkyl groups with 1 to 5 carbon atoms, inclusive.

The new compounds of this invention may be used therapeutically as the racemic mixtures of (+)- and (−)-forms, which are obtained by synthesis. They may also be resolved into the corresponding optically active modifications which, likewise, may be used in therapy. The compounds of this invention may be administered in the form of free bases or their salts with non-toxic acids. Some typical examples of these salts are the hydrobromide, hydrochloride, phosphate, sulphate, citrate, tartrate.

b. Pharmaceutical preparations

In clinical practice the compounds of the present, invention will normally be administered orally, rectally or by injection, in the form of pharmaceutical preparations comprising the active ingredient either as a free base or as a pharmaceutically acceptable non-toxic, acid addition salt, e.g., the hydrochloride, hydrobromide, lactate, acetate, sulphate, sulphamate and the like in association with a pharmaceutically acceptable carrier. Accordingly, terms relating to the novel compounds of this invention, whether generically or specifically, are intended to include both the free amine base and the acid addition salts of the free base, unless the context in which such terms are used, e.g., in the specific examples would be inconsistent with the broad concept. The carrier may be a solid, semisolid or liquid diluent or capsule. These pharmaceutical preparations constitute a further aspect of this invention. Usually the active substance will constitute between 0.1 and 95% by weight of the preparation, more specifically between 0.5 and 20% by weight for preparations intended for injection and between 2 and 50% by weight for preparations suitable for oral administration.

To produce pharmaceutical preparations containing a compound of the invention in the form of dosage units for oral application, the selected compound may be mixed with a solid pulverulent carrier, e.g., lactose, saccharose, sorbitol, mannitol, starches such as potato starch, corn starch or amylopectin, cellulose derivatives, or gelatine, and a lubricant such as magnesium stearate, calcium stearate, polyethylene glycol waxes, and the like, and then compressed to form tablets. If coated tablets are required, the cores, prepared as described above, may be coated with a concentrated sugar solution which may contain, e.g., gum arabic, gelatine, talcum, titanium dioxide, and the like. Alternatively, the tablet can be coated with a lacquer dissolved in a readily volatile organic solvent or mixture of organic solvents. Dyestuffs may be added to these coatings in order to readily distinguish between tablets containing different active substances of different amounts of the active compound.

For the preparation of soft gelatine capsules (pearl-shaped closed capsules) consisting of gelatine and for example, glycerol or similar closed capsules, the active substance may be admixed with a vegetable oil. Hard gelatine capsules may contain granulates of the active substance in combination with solid, pulverulent carriers such as lactose, saccharose, sorbitol, mannitol, starches (e.g., potato starch, corn starch or amylopectin), cellulose derivatives or gelatine.

Dosage units for rectal application can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions for example, solutions containing from about 0.2% to about 20% by weight of the active substance herein described, the balance being sugar and a mixture of ethanol, water, glycerol, and propyleneglycol. Optically, such liquid preparations may contain coloring agents, flavoring agents, saccharine and carboxymethylcellulose as a thickening agent.

Solutions for parenteral applications by injection can be prepared in an aqueous solution of a water-soluble pharmaceutically acceptable salt of the active substance preferably in a concentration of from about 0.5% to about 10% by weight. These solutions may also contain stabilizing agents and/or buffering agents and may conveniently be provided in various dosage unit ampoules.

Suitable peroral doses of the compounds of the invention are 2–20 mg, preferably 5–15 mg given 1 to 3 times a day, preferably 2 times a day.

c. Preferred embodiment

The preferred compounds of the invention have the formulas

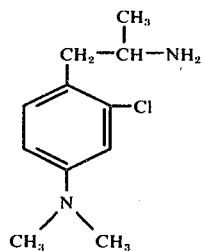
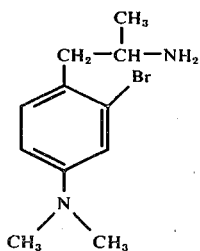

Preferably these compounds will be prepared and used in the form of their dihydrochloride salt.

d. Methods of preparation

A. Reduction of a substituted β-nitrostyrene of the formula

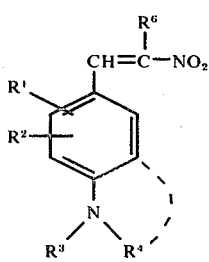

wherein $R^1$, $R^2$, $R^3$, $R^4$ and $R^6$ are as previously described, to form a compound of the formula I wherein $R^5$ is a hydrogen atom.

The reduction can be effected by means of an appropriate reducing agent such as lithium aluminum hydride or by catalytic reduction, or by other known reducing agents.

B. Reduction of a compound of the formula

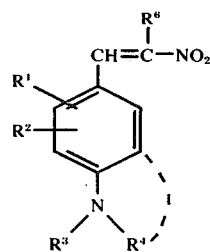

wherein $R^1$, $R^2$, $R^4$ and $R^6$ are as previously described and $R^{3'}$ is a lower aliphatic acyl group or a benzoyl group to form a compound of the formula I wherein $R^5$ is a hydrogen atom.

By the expression "lower aliphatic acyl group" in this application is to be understood aliphatic acyl groups

wherein R is a hydrogen atom or an alkyl group which contains 1 to 4 carbon atoms, inclusive.

Illustrative examples of lower aliphatic acyl groups are formyl, acetyl, propionyl, butyryl, isobutyl and valeryl.

C. Direct halogenation of a compound of the formula

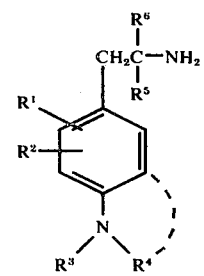

wherein $R^3$, $R^4$, $R^5$ and $R^6$ are as previously described and either $R^1$ or $R^2$ or both are hydrogen, to a compound of the formula I wherein $R^1$ or $R^2$ or both are a halogen atom.

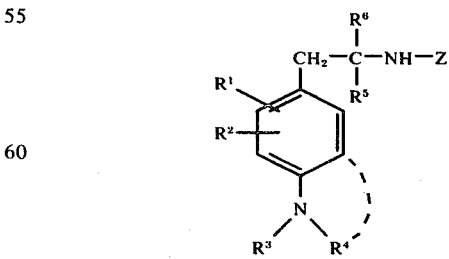

wherein $R^1$, $R^2$, $R^3$, $R^4$, $R^5$ and $R^6$ are as previously described and Z is lower aliphatic acyl group as defined on page 5, to form a compound of the formula I.

The hydrolysis is performed with a strong mineral acid.

e. Intermediates

A. For the preparation of the compounds of the formula I wherein R⁵ is a hydrogen atom it has been found that a compound of the formula

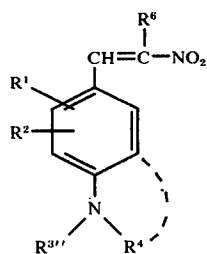

wherein R¹ and R² are the same or different and each represents a hydrogen atom, a lower alkyl group or a halogen atom, R³''' represents a lower alkyl group, a benzyl group, a lower aliphatic acyl group or a benzoyl group, R⁴ represents a hydrogen atom, a lower group, a benzyl group or a CH₂CH₂CH₂-bridge connected to the phenyl ring in ortho-position relative to the N-substituent and R⁶ represents a lower alkyl group, provided that R¹ and/or R² represents a lower alkyl group or a halogen atom when R³'' and R⁴ both represent a methyl or an ethyl group or when R³ represents an acetyl group and R⁴ a hydrogen atom, is a valuable starting material.

The compounds of the formula II are prepared as outlined below

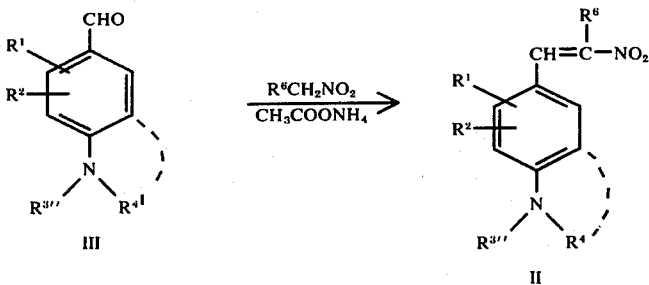

The intermediate nitrostyrenes of the formula II were prepared by a procedure involving condensation of the obtained aldehydes with excess nitroalkane, preferably in a suitable solvent, as for instance n-propyl alcohol, ethanol, acetic acid, etc., in the presence of a base, e.g., ammonium acetate.

Aldehydes of formula III wherein

R³''' = R³ represents a lower alkyl group or a benzyl group, and

R⁴ represents a hydrogen atom, a lower alkyl group, a benzyl group or a CH₂CH₂CH₂-bridge connected to the phenyl ring in ortho-position relative to the N-substituent are prepared in a step involving the formylation of the substituted aniline according to the Vilsmeyer-Haack reaction:

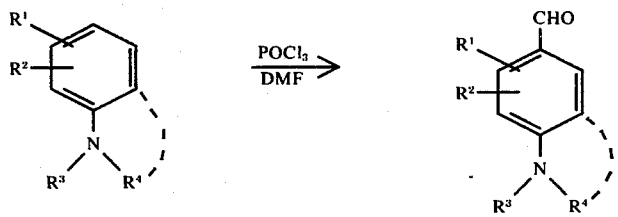

The formylation is effected by using a mixture of dimethylformamide and phosphorus oxychloride. Alternatively, the preparation is achieved by using a mixture of phosphorus tribromide and dimethylformamide (Acta Pharm. Suecica 7, 87, 1970).

Compounds other than dimethylformamide which may serve as the formylation agent are for instance N-methylformanilide or formamide. As catalysts other than phosphorus oxychloride and phosphorus tribromide may be used for instance, thionyl chloride, phosgene or aluminium chloride.

B. For the preparation of the compounds of the formula I it has been found that a compound of the formula

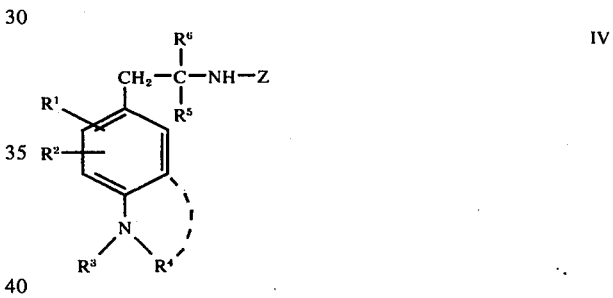

or a salt thereof, wherein R¹ and R² are the same or different and each represents a hydrogen atom, a lower alkyl or a halogen atom, R³ represents a lower alkyl group or a benzyl group, R⁴ represents a hydrogen atom, a lower alkyl group a benzyl group or a CH₂CH₂CH₂-bridge connected to the phenyl ring in ortho-position relative to the N-substituent, R⁵ represents a hydrogen atom or a methyl group, R⁶ is a lower alkyl group, and Z is a lower aliphatic acyl group, provided that R¹ and/or R² represents a lower alkyl group or a halogen atom when R³ is a methyl group, R⁴ is a methyl group and R⁵ represents a hydrogen atom is a valuable starting material.

The compounds of the formula IV can be prepared according to the reaction sequence

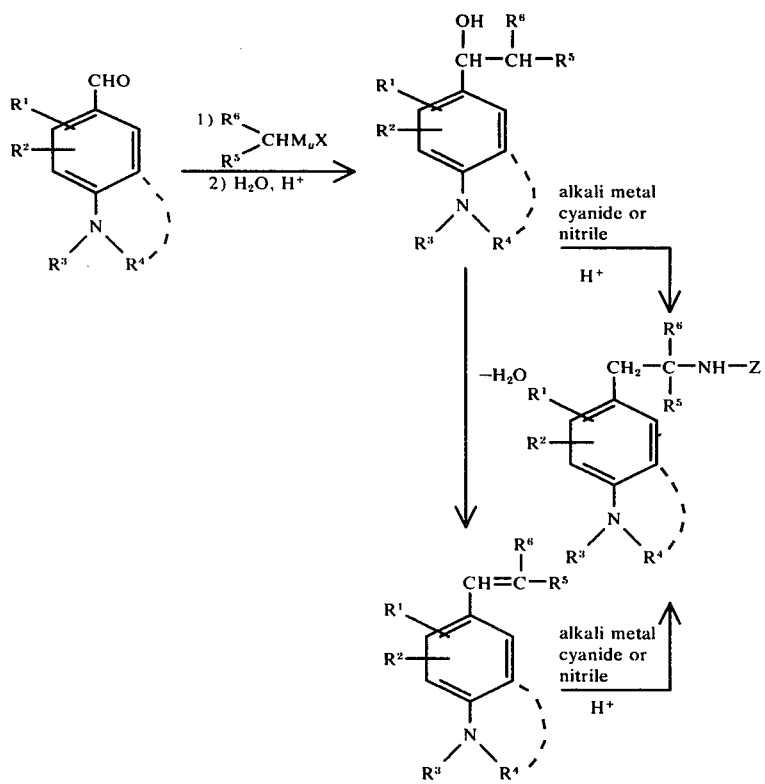

wherein $R^1$, $R^2$, $R^3$, $R^4$, $R^5$, $R^6$ and Z have the previously given definition and X is a bromide, chloride or iodide ion.

The aldehyde (prepared as described above) is treated with the Grignard reagent and the obtained alcohol is either directly converted to the amide IV by reaction with an alkali metal cyanide or a nitrile in the presence of a strong acid, e.g., sulphuric acid or via the dimethylvinyl compound which is reacted with an alkali metal cyanide or a nitrile in the presence of a strong acid, e.g., sulphuric acid to form the amide compound.

f. Working examples

Preparation of starting materials

Example 1.
—N,N-Dimethyl-3methyl-4-(2-nitropropenyl)aniline a. 4-Dimethylamino-2-methylbenzaldehyde 45 ml of phosphorus oxychloride is added dropwise while stirring and cooling in an ice bath to 145 ml of dimethylformamide. To this cooled solution is added by portions 67.5 g of N,N-dimethyl-m-toluidine. After addition the mixture is heated on a steam bath for 2 hours. The dark liquid is cooled and poured into 1.5 l of crushed ice. The solution is alkalized with sodium hydroxide. The crude, semisolid aldehyde (59.6 g) which separates is collected and purified by recrystallization from isopropyl ether.

Yield: 28.6 g, m.p. 65°–66°. Equiv. weight 163 (calc. 163.22)

The compound is also prepared as follows:

67.5 g of N,N-dimethyl-m-toluidine is dissolved in 250 ml of dimethyl formamide, and 35 ml of phosphorus tribromide is added dropwise with stirring and cooling in water. The temperature is not allowed to rise over 50°. The mixture is heated for 1.5 hour on a steam bath and poured into approximately 1.5 l of an ice water mixture. The solution is alkalized with sodium hydroxide and the crude product (46.9 g), which separates, is recrystallized from isopropyl ether. Yield: 20.5 g, m.p. 63–65°. A second recrystallization from the same solvent gives 14.6 g of the pure aldehyde, melting at 65°–66°.

b. N,N-Dimethyl-3-methyl-4-(2-nitropropenyl)aniline. A solution of 28.0 g of 4-dimethylamino-2methylbenzaldehyde, 20 ml of nitroethane and 15 g of ammonium acetate in 200 ml of 1-propanol is refluxed for 4 hours. The mixture is then poured into 1 l of ice water. The crude compound (30.2 g) is purified by recrystallization from ethanol-petroleum ether. Yield: 12.9 g, m.p. 75°–76°.

Analysis. Calculated for $C_{12}H_{16}N_2O_2$: C 65.44, H 7.32, N 12.72.

Found: C 64.7, H 7.38, N 12.7.

Example 2.
—N,N-Dimethyl-3-chloro-4-(2-nitropropenyl)aniline

A solution of 36.8 g of 2-chloro-4-dimethylaminobenzaldehyde, 18 ml of nitroethane and 15 g of ammonium acetate in 150 ml of absolute ethanol is refluxed for 2 hours. The mixture is then poured into 1.5 l of water, whereupon the compound separates as a viscous red oil, which crystallizes on scratching. Recrystallization from ethanol yields 18.0 g of the compound, melting at 93°–94°.

Analysis. Calculated for $C_{11}H_{13}ClN_2O_2$: C 54.89, H 5.44, Cl 14.73, N 11.64. Found: C 54.2, H 5.48, Cl 14.9, N 11.5.

Example 3.
N,N-Dimethyl-3,5-dichloro-4-(2-nitropropenyl)aniline a. N,N-Dimethyl-3,5-dichloroaniline. To a mixture of 40.5 g of 3.5-dichloroaniline and 62.0 g of sodium hydrogen carbonate in 200 ml of 50% aqueous dioxane is added dropwise with stirring and cooling in ice 60 ml of dimethyl sulphate (2 h). 100 ml of 30% sodium hydroxide solution is then added and the mixture is refluxed for 1 hour. After filtration the solution is extracted with ether. The extracts are dried over anhydrous sodium sulphate and the solvent is evaporated. The residue is recrystallized from methanol. Yield: 16.5 g, m.p. 53°–54°. Equiv. weight 193.5 (calc. 190.08).

b. 2,6-Dichloro-4-dimethylaminobenzaldehyde. 9 ml of phosphorus oxychloride is added dropwise while stirring and cooling in ice to a solution of 19.0 g of N,N-dimethyl-3,5-dichloroaniline in 29 ml of dimethylformamide. The mixture is heated for 1 hour on a steam bath and poured into ice. The solution is alkalized with sodium hydroxide and the crude product is filtered off.

Yield: 18.5 g. m.p. 152°–157°. The compound is purified by recrystallization from ethanol-dioxane. Yield: 13.9 g, m.p. 167°–168°.

Analysis. Calculated for $C_9H_9Cl_2NO$: C 49.56, H 4.16, Cl 32.51, N 6.42, O 7.34. Found: C 49.2, H 4.25, Cl 32.6, N 6.27, O 7.46.

c. N,N-Dimethyl-3,5-dichloro-4-(2-nitropropenyl)aniline. A solution of 13.8 g 2,6-dichloro-4-dimethylaminobenzaldehyde, 7 ml of nitroethane and 10.0 g of ammonium acetate in 100 ml of 1-propanol is refluxed for 24 hours. The mixture is then poured into 1 l of ice water. The precipitate is filtered off and washed with water. Yield: 16.8 g, m.p. 105°–110°. Recrystallization from aqueous ethanol gives 14.4 g of the analytically pure product, melting at 113°–114°.

Analysis. Calculated for $C_{11}H_{12}Cl_2N_2O_2$: C 48.02, H 4.40, Cl 25.77, N 10.18, O 11.63. Found: C 47.8, H 4.43, Cl 26.1, N 9.95, O 11.6.

Example 4.
—N-Methyl-6-(2-nitropropenyl)-1,2,3,4-tetrahydroquiniline a. N-Methyl-1,2,3,4-tetrahydroquinoline. To a mixture of 100 g of 1,2,3,4-tetrahydroquinoline and 100 g sodium hydrogen carbonate in 600 ml of 50% aqueous dioxane is added dropwise with stirring and cooling in ice 100 ml of dimethyl sulphate (2 h). After the addition the mixture is stirred over night at room temperature. 200 ml of 30% sodium hydroxide solution is then added and the mixture is refluxed for 1 hour. After filtration the solution is extracted with ether. The extracts are dried over anhydrous sodium sulphate and the solvent is evaporated. The residual oil (63.2 g) is distilled. Yield: 50.4 g, b.p. 108°–110°/10 mm. Equiv. weight 148 (calc. 147.22).

b. 6-Formyl-1-methyl-1,2,3,4-tetrahydroquinoline. 31 ml of phosphorus oxychloride is added dropwise stirring and cooling in ice into 100 ml of dimethylformamide. To the stirred and cooled solution is added by portions 50.0 g of N-methyl-1,2,3,4-tetrahydroquinoline. After the addition the mixture is heated on a steam bath for 1 hour. The liquid is cooled and poured into 1 l of crushed ice. The solution is alkalized with sodium hydroxide and extracted with ether. The extract is dried over anhydrous sodium sulphate and the solvent evaporated. The residual oil is distilled. Yield: 47.4 g, b.p. 175°–178°/6 mm. Equiv. weight 178 (calc. 175.23).

c. N-Methyl-6-(2-nitropropenyl)-1,2,3,4-tetrahydroquinoline.

A solution of 47.1 g of 6-formyl-1-methyl-1,2,3,4-tetrahydroquinoline, 24 ml of nitroethane and 20 g of ammonium acetate in 200 ml of 1-propanol is refluxed for 5 hours. The mixture is then poured into 1 l of ice water. The precipitated oil is extracted with ether and dried with anhydrous sodium sulphate. Evaporation of the solvent gives 54.8 g of a dark yellow oil, which, however, could not be recrystallized. The product is used directly, without further purification, in the subsequent step.

Example 5.
—N,N-Dimethyl-3-bromo-4-(2nitropropenyl)aniline a. 2-Bromo-4-dimethylaminobenzaldehyde. 14.5 ml of phosphorus oxychloride is added dropwise while stirring and cooling to a solution of 31.6 g of N,N-dimethyl-3-bromoaniline in 46 ml of dimethylformamide. The mixture is heated for 1 hour on a steam bath and poured into ice. The solution is alkalized with sodium hydroxide. The precipitate is filtered off and recrystallized from aqueous ethanol. Yield: 19.6 g, m.p. 81°–82°.

Analysis. Calculated for $C_9H_{10}BrNO$: C 47.39, H 4.42, Br 35.04, N 6.14, O 7.01. Found: C 47.1, H 4.38, Br 35.0, N 6.11, O 7.40.

b. N,N-Dimethyl-4-dimethylaminoenzaldehyde, 10 ml of nitroethane and 15 g of ammonium acetate in 100 ml of 1-propanol is refluxed for 7 hours. The mixture is then poured into 1 l of ice water. The precipitate is filtered off and purified by recrystallization from aqueous ethanol. Yield: 10.2 g, mp. 102°–103°.

Analysis. Calculated for $C_{11}H_{13}BrN_2O_2$: C 46.33, H 4.59, Br 28.03, N 9.82, O 11.22. Found: C 45.9, $H_{4.57}$, Br 28.0, N 9.63, O 11.3.

Example 6. N[α,α-dimethyl-β-(4-dimethylaminophenyl)ethyl]acetamide 9.2 ml of acetontrile is added dropwise at room temperature to a stirred solution 18.5 ml of concentrated sulphuric acid in 140 ml of acetic acid. 30.6 g of N,N-dimethyl-p-2′, 2′-dimethylvinylaniline is then added and the mixture is heated and stirred for 1 hour at 70°. The liquid is poured into crushed ice and the mixture is neutralized with sodium hydroxide (pH 6). The crude compound (29.8 g) is filtered off and purified by recrystallization from ethanol ligroin. Yield: 17.0 g, m.p. 156°–157°.

Analysis. Calculated for $C_{14}H_{22}N_2O$: C 71.75, H 9.46, N 11.96, O 6.83. Found: C 71.4, H 9.4, N 12.0, O 6.9.

Example 7.
—N,N-Dimethyl-3-chloro-4-(2nitro-1-butenyl)aniline

A solution of 36.8 g of 2chloro-4-dimethylaminobenzaldehyde, 25 ml of 1-nitropropane and 20 g of ammonium acetate in 150 ml of 1-propanol is refluxed for 15 hours. The mixture is then poured into 1.5 l of water whereupon the compound separates as a viscous red oil. Recrystallization twice from aqueous acetic acid yields 5.0 g of the compound, melting at 90°–91°.

Analysis. Calculated for $C_{12}H_{15}ClN_2O_2$: C 56.58, H 5.94, U 13.92, N 11.00, O 12.56. Found: C 56.8, H 5.6, Cl 14.0, N 10.9.

Preparation of end compounds

Example 8.
—2-Methyl-4-dimethylamino-α-methylphenethylamine dihydrochloride (Method A)

12.5 g of N,N-dimethyl-3-methyl-4-(2-nitropropenyl)aniline in 150 ml of dry ether is added to a stirred mixture of 9.1 g of lithium aluminum hydride in 200 ml of dry ether at such a rate that the solvent refluxes gently without external heating. The mixture is stirred and refluxed for 5 hours. 50 ml of saturated sodium sulphate solution is added dropwise with vigorous stirring and cooling in ice water. The mixture is filtered and the ethernal solution dried over anhydrous sodium sulphate. The dihydrochloride is precipitated from the solution by the addition of ether saturated with hydrogen chloride. The crude salt is purified by recrystallization from ethanol-isopropyl ether. Yield: 12.6 g, m.p. 205°–207°. A second recrystallization from the same solvent gives 11.0 g of the compound, melting at 208°–209°.

Example 9 —4-Ethylamino-α-methylphenethylamine dihydrochloride (Method b)

11.0 g of 4-(2-nitropropenyl)acetanilide dissolved in 150 ml of dry tetrahydrofuran is added dropwise to a stirred mixture of 11.0 of lithium aluminum hydride in 200 ml of dry ether. After the addition the reaction mixture is stirred and refluxed for 4 hours. 60 ml of saturated sodium sulphate solution is added carefully with stirring and cooling. The mixture is filtered and the ethereal solution is evaporated. The residue is dissolved in dilute hydrochloric acid and the solution is shaken with ether. The acidic layer is alkalized with sodium hydroxide and the solution is extracted with ether. After drying over solid sodium hydroxide the extract is evaporated. The residue is distilled to obtained 4.7 g of free base boiling at 97°–100°/0.03 mm. The free amine is converted to the dihydrochloride by dissolving the base in ether and treating the solution with an excess of dry hydrogen chloride. Recrystallization of the obtained precipitate yields 4.8 g of the pure salt, melting at 184°–185°.

Example 10
—2-Chloro-4dimethylamino-α-methylphenethylamine dihydrochloride (Method A)

A solution of 12.0 g of N,N-dimethyl-3-chloro-4-(2-nitropropenyl)aniline in 150 ml of dry tetrahydrofuran is added dropwise with stirring to 8.0 g of lithium aluminium hydride in 200 ml of dry ether. After the addition the reaction mixture is refluxed for 5 hours. 40 ml of saturated sodium sulphate solution is added by portions and the mixture is filtered. The filtrate is dried with anhydrous sodium sulphate and acidified with hydrogen chloride in ether. The precipitate is removed by filtration and recrystallized from ethanol-isopropyl ether. Yield: 9.3 g, m.p. 187°–191°. A second recrystallization from the same solvent yields 8.1 g of the pure compound, melting at 193°–195°.

Example 11
—2,6-Dichloro-4-dimethylamino-α-methylphenethylamine dihydrochloride (Method A)

A solution of 13.7 g of N,N-dimethyl-3,5-dichloro-4-(2-nitropropenyl)aniline in 150 ml of dry tetrahydrofuran is added dropwise with stirring to 8.0 g lithium aluminum hydride in 200 ml of dry ether. The mixture is then refluxed for 4 hours. 40 ml of saturated sodium sulphate solution is added dropwise and the mixture is filtered. The filtrate is dried over anhydrous sodium sulphate and acidified with hydrogen chloride. The precipitated salt is filtered off and washed with ether. Yield: 15.2 g, m.p. 195°–197°. The product is recrystallized from aqueous ethanol-isopropyl ether. Yield: 11.9 g, m.p. 199°–200°.

Example 12
—3-Bromo-4-dimethylamino-α-methylphenethylamine dihydrochloride (Method C)

To a mixture of 2.51 g of 4-dimethylamino-α-methylphenethylamine dihydrochloride and 5.0 g of anhydrous sodium acetate in 50 ml of acetic acid is added dropwise with stirring a solution of 0.51 ml of bromine in 50 ml of acetic acid. The mixture is stirred at room temperature for 2 hours. The solvent is evaporated and the residue dissolved in 200 ml of water. The solution is alkalized with sodium hydroxide and extracted with ether. The ether extract is dried over anhydrous sodium sulphate and acidified with hydrogen chloride in ether. The precipitate is filtered off and recrystallized from ethanol-ethyl acetate. Yield: 2.3 g, m.p. 190°–191°.

Example 13
—6-(2-Aminopropyl)-1-methyl-1,2,3,4-tetrahydroaquinoline dihydrochloride (Method A)

A solution of 11.6 g of crude Nmethyl-6-(2-nitropropenyl)-1,2,3,4-tetrahydroquinoline in 150 ml of dry ether is added dropwise with stirring to 8.0 g of lithium aluminum hydride in 150 ml of ether. The reaction mixture is refluxed for 4 ml of saturated sodium sulphate solution is added dropwise and the mixture is filtered. The filtrate is acidified with hydrogen chloride in ether. The precipitated syrupy product is dissolved in 250 ml of water and alkalized with sodium hydroxide. The solution is extracted with ether and the extract is dried over anhydrous sodium sulphate. The solvent is evaporated and the residual oil is distilled. Yield: 3.3 g, b.p. 135°–137°/0.07 mm. The base is dissolved in ether and the dihydrochloride is precipitated from the solution by the addition of an excess hydrogen chloride in ether. The precipitated salt is recrystallized from ethanol-isopropyl ether.

Yield: 3.3 g, m.p. 221°–222°.

Example 14
—2-Bromo-4-dimethylamino-α-methylphenethylamine dihydrochloride (Method A)

A solution of 10.0 g of N,N-dimethyl-3-bromo-4-(2-nitropropenyl)aniline in 100 ml of dry tetrahydrofuran is added dropwise with stirring to 8.0 g of lithium aluminum hydride in 200 ml of dry ether. After the addition the reaction mixture is refluxed for 4 hours. 40 ml of saturated sodium sulphate solution is then added by portions and the mixture is filtered. The filtrate is acidified with hydrogen chloride in ether. The precipitated syrupy product is dissolved in water. The solution is washed with ether and alkalized with sodium hydroxide. The separated oil is extracted with ether and the ether extracted is dried over anhydrous sodium sulphate. The solution is acidified with hydrogen chloride in ether and the semi-solid precipitate is filtered off and recrystallized from ethanol-isopropyl ether. Yield: 8.2 g, m.p. 195°–196°.

Example 15 — 4-Dimethylamino-α, α-dimethylphenethylamine dihydrochloride (Method D)

A solution of 3.5 g of N-[α,α-dimethyl-β-(4-dimethylaminophenyl) ethyl]acetamide in a mixture of 25 ml of water and 25 ml of concentrated hydrochloric acid is reluxed for 16 hours. The solution is then evaporated under reduced pressure and the residue is recrystallized twice from methanol isopropyl ether. Yield: 1.1 g, m.p. 239°–240,5°.

In Table 1 are given data for some end compounds of this invention including those described in Examples 8–15.

In Table 2 are given data for some intermediates of this invention including those described in Examples 1–7. The products of this table, not exemplified above, are analogously prepared. The intermediate oily nitro compounds are used directly without further purification.

Table 2

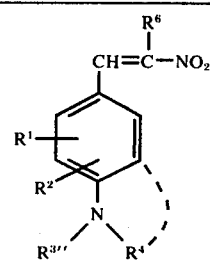

| $R^1$ | $R^2$ | $R^{3''}$ | $R^4$ | $R^6$ | M.p. °C | Described in Ex. No. |
|---|---|---|---|---|---|---|
| 3-CH$_3$ | H | CH$_3$ | CH$_3$ | CH$_3$ | 75–76 | 1 (b) |
| 2-CH$_3$ | H | CH$_3$ | CH$_3$ | CH$_3$ | Oil | — |
| H | H | CH$_3$ | C$_2$H$_5$ | CH$_3$ | Oil | — |
| H | H | C$_2$H$_5$CH$_2$ | C$_6$H$_5$CH$_2$ | CH$_3$ | Oil | — |
| 3-Cl | H | CH$_3$ | CH$_3$ | CH$_3$ | 93–94 | 2 |
| 3-Cl | 5-Cl | CH$_3$ | CH$_3$ | CH$_3$ | 113–114 | 3 (c) |
| 3-Br | H | CH$_3$ | CH$_3$ | CH$_3$ | 102–103 | 5 (b) |
| 3-Cl | H | CH$_3$ | CH$_3$ | C$_2$H$_5$ | 90–91 | 7 |

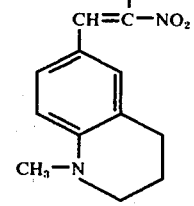

Oil — 4 (c)

Table 1

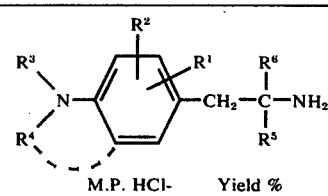

| Described in Ex. No. | $R^1$ | $R^2$ | $R^3$ | $R^4$ | $R^5$ | $R^6$ | M.P. HCl-salt °C / B.P. base/mm °C | Yield % HCl-salt / Base | Recrystallized from | \multicolumn{4}{c}{HCl-salt, analysis: Calculated % / Found %} |
|---|---|---|---|---|---|---|---|---|---|---|---|---|---|

| Described in Ex. No. | $R^1$ | $R^2$ | $R^3$ | $R^4$ | $R^5$ | $R^6$ | M.P. HCl-salt °C / B.P. base/mm °C | Yield % HCl-salt / Base | Recrystallized from | C | H | Cl | N |
|---|---|---|---|---|---|---|---|---|---|---|---|---|---|
| 8 | 2-CH$_3$ | H | CH$_3$ | CH$_3$ | H | CH$_3$ | 208–209 | 83 | ethanol/isopropyl ether | 54.34 / 54.4 | 8.36 / 8.37 | 26.73 / 26.6 | 10.56 / 10.5 |
| — | 3-CH$_3$ | H | CH$_3$ | CH$_3$ | H | CH$_3$ | 232–233 / 101–105°/0.5 | — / 43 | ethanol/ethyl acetate | 54.34 / 54.2 | 8.36 / 8.34 | 26.73 / 26.4 | 10.56 / 10.5 |
| 9 | H | H | H | C$_2$H$_5$ | H | CH$_3$ | 184–185 / 97–100/0.03 | — / 53 | ethanol/isopropyl ether | 52.59 / 52.6 | 8.03 / 8.06 | 28.23 / 28.0 | 11.15 / 11.2 |
| — | H | H | CH$_3$ | C$_2$H$_5$ | H | CH$_3$ | 209–210 / 120–123/0.04 | — / 61 | ethanol/isopropyl ether | 54.34 / 54.1 | 8.36 / 8.43 | 26.73 / 26.4 | 10.56 / 10.5 |
| — | H | H | C$_2$H$_5$ | C$_2$H$_5$ | H | CH$_3$ | 219–220 / 98–102/0.3 | — / 89 | ethanol/isopropyl ether | 55.91 / 55.6 | 8.66 / 8.62 | 25.41 / 25.4 | 10.03 / 9.94 |
| — | H | H | C$_6$H$_5$CH$_2$ | C$_6$H$_5$CH$_2$ | H | CH$_3$ | 156–157 | 50 | ethanol/ethyl acetate | 68.48 / 67.8 | 7.00 / 7.01 | 17.58 / 17.1 | 6.95 / 6.91 |
| 10 | 2-Cl | H | CH$_3$ | CH$_3$ | H | CH$_3$ | 193–195 | 65 | ethanol/isopropyl ether | 46.25 / 46.1 | 6.70 / 6.89 | 37.24 / 37.5 | 9.81 / 9.73 |
| 11 | 2-Cl | 6-Cl | CH$_3$ | CH$_3$ | H | CH$_3$ | 199–200 | 95 | aqueous ethanol/ isopropyl ether | 41.27 / 41.7 | 5.67 / 5.84 | 44.31 / 44.1 | 8.75 / 8.60 |
| 12 | 3-Br | H | CH$_3$ | CH$_3$ | H | CH$_3$ | 190–191 | 70$^a$ | ethanol/ethyl acetate | 40.02 / 39.7 | 5.80 / 5.81 | 21.48 / 21.4 | 8.49 / 8.42 |
| 14 | 2-Br | H | CH$_3$ | CH$_3$ | H | CH$_3$ | 195–196 | 70 | ethanol/isopropyl ether | 40.02 / 40.6 | 5.80 / 5.95 | 21.48 / 21.5 | 8.49 / 8.55 |
| 15 | H | H | CH$_3$ | CH$_3$ | CH$_3$ | CH$_3$ | 239.5–240.5 | 28 | methanol/isopropyl ether | 54.34 / 53.5 | 8.36 / 8.40 | 26.73 / 26.3 | 10.56 / 10.4 |
| — | 2-Cl | H | CH$_3$ | CH$_3$ | H | C$_2$H$_5$ | 229–230 | 85 | ethanol/isopropyl ether | 48.09 / 47.8 | 7.06 / 7.13 | b | 9.35 / 9.23 |
| 13 | | | | | | | 221–222 / 135–140/0.07 | — / 32 | ethanol/isopropyl ether | 56.32 / 55.7 | 8.0 / 8.15 | 25.58 / 25.3 | 10.11 / 9.91 |

$^a$ Cl-Br: Calc. 45.69; found 45.2
$^b$ Cl- Calc. 93.66; found 93.2 g. Pharmacological tests

It is not possible by experimental means to induce depressions in laboratory animals. In order to evaluate a possible anti depressive effect on new substances biochemical-pharmacological test methods must be resorted to. One such method, which seems to give a good indication of the potential anti depressive effects of the test substances, is described in Europ. J. Pharmacol. 17, 107, 1972. This method involves the measurement of the potentiation of the syndromes produced by 5-hydroxytryptophan (5-HTP) in a laboratory animal.

The lack of euphoric effects, that is lack of central stimulatory activity, is tested by measuring the motor activity in mice after administration of the test substance.

Potential anxiolytic activity is texted by measuring the antiaggressivity in isolated mice after administration of the test substance. In this test not amphetamine but Valium — a well-known anxiolytic substance — is used as a reference.

5-HTP response potantiation test

Inhibition of the uptake of 5HT potentiates the effects of administered 5-hydroxdytrptophan (5-HTP) probably by increasing the amount of 5-HT at the receptor. Three mice are given the test drugs 1 hour (or 4, 24 hours) before dl-5-HTP, 90 mg/kg i.v. 5-HTP alone gives only a weak behavioral syndrome but in pretreated mice there is seen a characteristic behavioral syndrome, which comes within 5 minutes: tremor, lordosis, abduction of the hind-legs, head-twitches.

The absence or presence of respective syndrome is scored in groups of 10 mice. The compound was administered in at least five doses and the quantal responses were analysed by probit analysis and $ED_{50}$ determined according to the method of Litchfield and Wilcoxon.

Motor activity in mice

The exploratory activity of mice was recorded in a locomotion cage in which the movements were counted each time the animals cross-circuits an electrical current in the bottom plate. The activity was recorded for 10 minutes 1 hour after the administration of the drug. The animals were tested individually. Groups of six mice were used and the mice were only used once. The activity was expressed in percent of the activity of control groups ran simultaneously. The compounds were administered in at least four doses. The increase (+) or decrease (−) of the activity compared to control groups was determined from log dose response curves.

Aggressive behavior in mice

Male mice kept isolated for 3 weeks or longer develop an aggressive behavior when caged together. The method used follows that of Valzelli et al. (Europ. J. Pharmacol. 2, 144, 1967), with the exception that two mice were tested on each other. The aggressiveness was scored during a 5 min test according to the following schedule:

0 the animals show no interest in each other except occasional nosing 25 frequent vigorous nosing and tail rattling, the animals assume a fighting position and occasionally attack each other — no more than 3–4 times in the 5 min period 50 tail rattling, powerful attacks — no more than 10 times in the test period 75 the animals follow their partners, attacking and biting for most of the time 100 attacks over the entire period.

Controls administered with the solvent were tested, the repeated testing did not influence the aggressiveness. The animals were used for several experiments but with intervals of at least 1 week. Groups of 10 mice were used.

$ED_{50}$ is the dose which reduces the aggressiveness score by 50%.

Table 3

Pharmacological effects of 4-aminoamphetamine derivatives

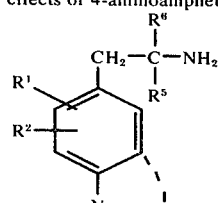

| Compound R¹ | R² | R³ | R⁴ | R⁵ | R⁶ | Potentiation of 5-HTP $ED_{50}$ mg/kg i.p. | Motor Activity + = increase − = decrease 0 = no effect | Antiaggressive behaviour in mice $ED_{50}$ mg/kg i.p. |
|---|---|---|---|---|---|---|---|---|
| Valium | | | | | | | | 2.5 |
| Amphetamine | | | | | | >5 | +++ | X |
| P-Aminoamphetamine | | | | | | 11.5 | | |
| P-Chloroamphetamine | | | | | | 0.8 | ++ | 0.3 |
| H | H | C₂H₅ | C₂H₅ | H | CH₃ | 2 | − | 5–10 |
| H | 2-Cl | CH₃ | CH₃ | H | CH₃ | 0.25 | − | 2.5–5 |
| H | H | C₂H₅ | H | H | CH₃ | 1 | | 1.25 |
| H | 2-CH₃ | CH₃ | CH₃ | H | CH₃ | 0.6 | − | 2.5–5 |
| H | H | C₂H₅ | CH₃ | H | CH₃ | 0.7 | | <5 |
| H | 3-Br | CH₃ | CH₃ | H | CH₃ | 1 | | >5 |
| 2-Cl | 6-Cl | CH₃ | CH₃ | H | CH₃ | 0.1 | − | >5 |
| H | H | CH₃ | —(CH₂)₃— | H | CH₃ | 1.5 | | >5 |

| H | 2-Br | CH₃ | CH₃ | H | CH₃ | 0.1 | |
| H | H | CH₃ | CH₃ | CH₃ | CH₃ | 2.5 | 0 |
| H | 2-Cl | CH₃ | CH₃ | H | C₂H₅ | 0.25 | 0 |

X Not tested, due to interference with motor activity

As can be seen from the test values of Table 3 the tested substances differ considerably in activity from amphetamine both qualitatively and quantitatively. In contrast to amphetamine the tested compounds of the invention strongly potentiate the 5-HTP response. Furthermore, the tested compounds lack the central stimulation which is pronounced after amphetamine and p-chloroamphetamine. The tested compounds rather give a weak sedation. Thus, the potential antidepressive activity as indicated by the potentiation of 5-HPT and the lack of central stimulatory activity may give the compounds of this invention value as potential antidepressive agents.

The tested compounds antagonize the aggressive behavior of male mice which have been kept isolated for one month or more. Many of the compounds are at least as active as Valium in this test which may indicate that these compounds may have therapeutic value as anxiolytic compounds.

We claim:

1. A pharmaceutical preparation which comprises a therapeutically effective amount for the treatment of depressive states or alleviating anxiety of an active ingredient of the formula

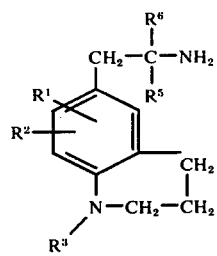

or a pharmaceutically acceptable salt thereof, in which formula $R^1$ and $R^2$ are the same or different and each represents a hydrogen atom, a lower alkyl group or a halogen atom, $R^3$ represents a lower alkyl group or a benzyl group, $R^5$ represents a hydrogen atom or a methyl group, and $R^6$ represents a lower alkyl group, in association with a pharmaceutically acceptable carrier.

2. A method for the alleviation of anxiety comprising administering to a host suffering from such ailment, a therapeutically effective amount for alleviation of anxiety of a compound of the formula

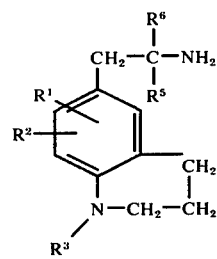

or a pharmaceutically acceptable salt thereof, in which formula $R^1$ and $R^2$ are the same or different and each represents a hydrogen atom, a lower alkyl group or a halogen atom, $R^3$ represents a lower alkyl group or a benzyl group, $R^5$ represents a hydrogen atom or a methyl group, and $R^6$ represents a lower alkyl group.

3. A method for the treatment of depression comprising administering to a host suffering from such ailment, a therapeutically effective amount for relieving the depression of a compound of the formula

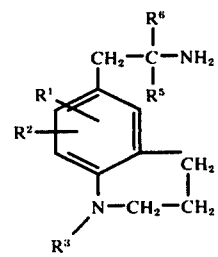

or a pharmaceutically acceptable salt thereof, in which formula $R^1$ and $R^2$ are the same or different and each represents a hydrogen atom, a lower alkyl group or a halogen atom, $R^3$ represents a lower alkyl group or a benzyl group, $R^5$ represents a hydrogen atom or a methyl group, and $R^6$ represents a lower alkyl group.

4. A pharmaceutical preparation which comprises a therapeutically effective amount for the treatment of depressive states or alleviating anxiety of an active ingredient of the formula

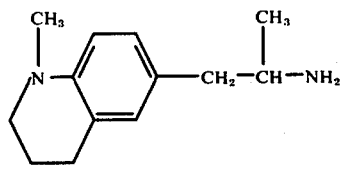

or a pharmaceutically acceptable salt thereof, in association with a pharmaceutically acceptable carrier.

5. A method for alleviation of anxiety comprising administering to a host suffering from such ailment, a therapeutically effective amount for alleviation of anxiety of the compound of the formula

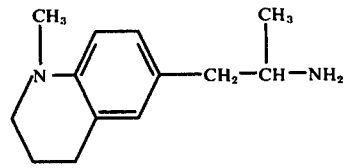

or a pharmaceutically acceptable salt thereof.

6. A method for the treatment of depression comprising administering to host suffering from such ailment, a therapeutically effective amount for relieving the depression of the compound of the formula

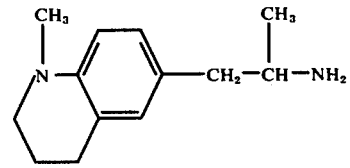

or a pharmaceutically acceptable salt thereof.

* * * * *

UNITED STATES PATENT OFFICE
CERTIFICATE OF CORRECTION

Patent No. 4,000,280      Dated December 28, 1976

Inventor(s) Gösta Lennart Florvall et al.

It is certified that error appears in the above-identified patent and that said Letters Patent are hereby corrected as shown below:

Column 1, line 63, "of" should be -- or --.

Column 4, line 68, "page 5" should be -- above --.

Column 5, line 38, "$R^7$" should be -- $R^1$ --.

Column 5, line 40, "$R^3$" should be -- $R^{3''}$ --.

Column 7, line 52, add period after "4-Dimethylamino-2-methyl-benzaldehyde".

Column 9, line 61, before "stirring" insert -- while --.

Column 10, line 59, "2chloro-" should be -- 2-chloro- --.

Column 11, line 14, "ethernal" should be -- etheral --.

Column 12, line 30, "Nmethyl-" should be -- N-methyl- --.

Column 12, line 34, "4 ml of saturated" should be -- 4 hours. 40 ml of saturated --.

Column 15, line 24, "5HT" should be -- 5-HT --.

UNITED STATES PATENT OFFICE
CERTIFICATE OF CORRECTION

Patent No. 4,000,280  Dated December 28, 1976

Inventor(s) Gösta Lennart Florvall et al.

It is certified that error appears in the above-identified patent and that said Letters Patent are hereby corrected as shown below:

Column 15, line 25, "5-hydroxdytrptophan" should be -- 5-hydroxytryptophan --.

Signed and Sealed this twelfth Day of July 1977

[SEAL]

Attest:

RUTH C. MASON
Attesting Officer

C. MARSHALL DANN
Commissioner of Patents and Trademarks